(12) United States Patent
LeJeune et al.

(10) Patent No.: US 6,673,565 B2
(45) Date of Patent: *Jan. 6, 2004

(54) ENZYMATIC POLYMERIC SENSORS

(75) Inventors: Keith E. LeJeune, Pittsburgh, PA (US);
Alan J. Russel, Wexford, PA (US)

(73) Assignee: Agentase, LLC, Pittsburgh, PA (US)

( * ) Notice: Subject to any disclaimer, the term of this patent is extended or adjusted under 35 U.S.C. 154(b) by 12 days.

This patent is subject to a terminal disclaimer.

(21) Appl. No.: 09/952,112

(22) Filed: Sep. 14, 2001

(65) Prior Publication Data

US 2002/0150959 A1 Oct. 17, 2002

Related U.S. Application Data

(63) Continuation-in-part of application No. 09/441,596, filed on Nov. 17, 1999, now Pat. No. 6,291,200.

(51) Int. Cl.[7] .................. C12Q 1/46; C12Q 1/42; C12Q 1/37; C12Q 1/34
(52) U.S. Cl. .................. 435/20; 435/21; 435/22; 435/24; 435/18; 435/15; 435/16; 435/4; 435/283.1; 435/289.1
(58) Field of Search .................. 435/20, 21, 22, 435/24, 18, 15, 16, 4, 283.1, 289.1

(56) References Cited

U.S. PATENT DOCUMENTS

| | | | | |
|---|---|---|---|---|
| 3,791,927 A | 2/1974 | Forgione | .................. | 195/63 |
| 4,324,858 A | 4/1982 | Goodson | .................. | 435/20 |
| 4,525,704 A | 6/1985 | Campbell | .................. | 204/403 |
| 5,272,061 A | 12/1993 | Hasselberg | .................. | 435/20 |
| 5,858,186 A | 1/1999 | Glass | .................. | 204/403 |
| 5,919,576 A | 7/1999 | Hui | .................. | 428/545 |
| 5,945,343 A | 8/1999 | Munkholm | .................. | 436/108 |
| 5,958,786 A | 9/1999 | Munkholm | .................. | 436/98 |
| 6,001,556 A | 12/1999 | Charych | .................. | 435/5 |
| 6,291,200 B1 * | 9/2001 | LeJeune et al. | .................. | 435/20 |

OTHER PUBLICATIONS

Rogers, K. R., Biosensors Bioelectronics, 10, 533 (1995).
Parente, A. H., Marques, E. T. Jr., Appl. Biochem. Biotechnol. 37, 3, 267 (1992).
Yang, S., Atanasov, P., Wilkins, E., Ann. Biomed. Eng., 23, 6, 833 (1995).
Turner, A. P. F., Sensors Actuators, 17, 433 (1989).
Evtugyn, G. A., Budnikov, H. C., Kolskaya, Talanta, 46, 465 (1998).
Copy of Communication from the European Patent Office enclosing Supplementary European Search Report corresponding to a related case (i.e., the parent case) (Jan. 23, 2003).
Otto S. Wolfbeis et al. "Recent Progress in Optical Oxygen Sensing". Optical Fibers in Medicine III, Los Angeles, CA, Jan. 13–16, 1988, vol. 906, 42–48.
Alumni Newsletter, University of Pittsburgh, Department of Chemical and Petroleum Engineering, Online 1999.
Young Ae Cho et al. "Fabrication of Butyrylcholineesterase Sensor Using Polyurethane–Based Ion–Selective Membranes". Biosensors & Bioelectronics. England Apr. 30, 1999, vol. 14, No. 4, Apr. 30, 1999, 387–390.
Jaroslav Katrlik et al. "Composite Alcohol Biosensors Based On Solid Binding Matrix". Biosensors & Bioelectronics, Feb. 1, 1998. Elsevier, UK, vol. 13, No. 2, 181–191.

* cited by examiner

*Primary Examiner*—Louise N. Leary
(74) *Attorney, Agent, or Firm*—Bartony & Hare, LLP (57) ABSTRACT

A sensor for detecting an analyte enzyme includes at least one substrate compound and at least one indicator compound selected to produce a measurable change of state as a result of the interaction of the substrate and at least one target or analyte enzyme. Each of the indicator(s) and substrate(s) are incorporated within a single polymer.

15 Claims, 4 Drawing Sheets

Reaction schematic of biopolymer synthesis.

Figure 1. Reaction schematic of biopolymer synthesis.

Figure 2a. Urease induced base production in urea-containing buffer solutions.

Figure 2b. BChE induced acid production in butyrylcholine buffer solutions.

Figure 3. BChE-polymer inhibition with DMMP.

Figure 4. Detection of paraoxon at a surface using BChE-containing polymers.

ENZYMATIC POLYMERIC SENSORS

RELATED REFERENCE

The present application is a continuation in part of allowed U.S. patent application Ser. No. 09/441,596, filed Nov. 17, 1999 now U.S. Pat. No. 6,291,200, the disclosure of which is incorporated herein by reference.

BACKGROUND OF THE INVENTION

The present invention relates to (i) enzyme-containing polymeric sensors, and, especially, to sensors in which an enzyme or enzymes and an indicator compound or indicator compounds are incorporated within a common or single polymer matrix and to (ii) substrate-containing polymeric sensors, and especially, to sensors in which a substrate compound or substrate compounds and an indicator compound or indicator compounds are incorporated within a common or single polymer matrix.

Enzymatic proteins are remarkable natural catalysts that selectively catalyze many reactions under relatively mild reaction conditions. Enzymes also offer the potential to perform sterio- and regio-selective reactions not readily accomplished with conventional chemistry. As used herein, the term "enzyme" refers generally to proteins that catalyze biochemical reactions. These "biopolymers" include amide-linked amino acids and typically have molecular weights of 5,000 or greater. A compound for which a particular enzyme catalyzes a reaction is typically referred to as a "substrate" of the enzyme.

In general, six classes or types of enzymes (as classified by the type of reaction that is catalyzed) are recognized. Enzymes catalyzing reduction/oxidation or redox reactions are referred to generally as EC 1 (Enzyme Class 1) Oxidoreductases. Enzymes catalyzing the transfer of specific radicals or groups are referred to generally as EC 2 Transferases. Enzymes catalyzing hydrolysis are referred to generally as EC 3 hydrolases. Enzymes catalyzing removal from or addition to a substrate of specific chemical groups are referred to generally as EC 4 Lyases. Enzymes catalyzing isomeration are referred to generally as EC 5 Isomerases. Enzymes catalyzing combination or binding together of substrate units are referred to generally as EC 6 Ligases.

Enzymes have been known since the early 1960's to be useful tools for detecting the presence of chemical species. Rogers, K. R., *Biosensors Bioelectronics*, 10, 533 (1995). Generally all enzymatic biosensors function by one of two methods. The enzyme either converts an undetectable compound of interest into another or series of compounds which can be detected with a chemical-based sensor or the enzyme is inhibited by the presence of the compound of interest and the enzyme inhibition is linked to a measurable quantity.

Enzymatic biosensors have been designed to detect a variety of different compounds such as glucose, creatinine, urea, and cholinesterase inhibitors. Parente, A. H., Marques, E. T. Jr.,*Appl. Biochem. Biotechnol.* 37, 3, 267 (1992); Yang, S., Atanasov, P., Wilkins, E., *Ann. Biomed. Eng.,* 23, 6, 833 (1995). U.S. Pat. No. 5,858,186 describes a urea-based biosensor in which substrate hydrolysis is monitored with a pH electrode. U.S. Pat. Nos. 5,945,343 and 5,958,786 describe enzyme-based sensors in which a fluorophere is immobilized in a first polymer layer and an enzyme is separately immobilized in a second polymer layer. The fluorophere layer fluoresces in the presence of ammonia, which is enzymatically produced from urea and creatinine (respectively, with respect to U.S. Pat. Nos. 5,945,343 and 5,958,786). In addition, U.S. Pat. No. 4,324,858 describes the immobilization of cholinesterase within a porous, dry material for the colormetric detection of organophosphorus pesticides and nerve agents. U.S. Pat. No. 4,525,704 describes the use of cholinesterases and electrical currents in detecting toxic gases.

Independent of the use thereof, enzyme-based biosensors are often limited in practical application by a number of factors. For example, the process of immobilizing the enzymes using highly specialized synthesis protocols is often expensive and time consuming. Moreover, the sensor often requires specialized electrical equipment to be used in conjunction with the immobilized enzyme, such as a pH meter or oxygen electrode. Turner, A. P. F., *Sensors Actuators,* 17, 433 (1989). The shelf-life, thermal stability, and reusability of enzymatic sensors is often problematic for practical application of the technology. Also, many enzyme-based sensors do not exhibit sufficient sensitivity toward the target compound to monitor the compound over a relevant concentration range. Evtugyn, G. A., Budnikov, H. C., Kolskaya, *Talanta,* 46, 465 (1998).

It is very desirable to develop improved enzyme-based sensors that reduce or eliminate the problems with current enzyme-based sensors.

SUMMARY OF THE INVENTION

In one aspect, the present invention provides a sensor for detecting the presence of at least one analyte. The sensor includes at least one enzyme that is selected to either (i) catalyze a reaction of the analyte to chemically convert the analyte to a product compound or (ii) be inhibited by the analyte in the presence of a substrate compound. The sensor also includes at least one indicator compound selected to produce a measurable change of state as a result of the interaction of the analyte and the enzyme. Each of the enzyme and the indicator compound are incorporated within a single polymer. Any polymer capable of retaining an enzyme and indicator compound that provides the incorporated/immobilized species with access to substrate, analyte, and/or the reaction products and is capable of undergoing a physical property change induced by the indicator compound is suitable for use in the present invention. The enzyme and/or the indicator compound can be added to a preexisting polymer or the polymer can be synthesized in the presence of the enzyme and/or the indicator compound to incorporate the enzyme and/or the indicator compound in the polymer.

In general, in the case that the analyte is converted to a product compound in a reaction catalyzed by the enzyme (that is, case (i), in which the analyte is a substrate of the enzyme), the indicator compound may be sensitive to the presence of the product compound and will produce a measurable change of state in the presence of the product compound.

In the case that the analyte inhibits the enzyme (case (ii), in which the analyte is not a substrate of the enzyme) the indicator compound may be sensitive to a product of the reaction of a substrate compound of the enzyme. In case (ii), the substrate compound is preferably added to the environment. If the indicator compound produces no change of state or a change of state that is less in degree than expected with an uninhibited enzyme, it is an indication of the presence of the analyte. Thus, enzyme inhibitors are detected by first incubating the enzyme and indicator compound-containing polymer within a sample of questionable nature. A "developing solution" containing the enzyme's substrate is later applied. The absence of a state transition yields a positive indication of inhibition and the presence of the target compound.

The indicator compound may, for example, be a dye that undergoes an observable change of state (for example, a change in optical properties/color) as a result of the interaction of the enzyme and the analyte. Preferably, such a dye changes optical properties in a manner that is visible to the human eye. The indicator compound may be chemically bonded to the polymer or physically entrapped therein. An example of a suitable polymer for use in the present invention is polyurethane.

The enzyme is preferably chemically bonded to the polymer, but can also be physically entrapped within the polymer. More preferably, the enzyme is covalently bonded to the polymer. In one embodiment, the enzyme is a hydrolase enzyme and the indicator compound is a dye that changes color as a function of pH. Examples of suitable hydrolase enzymes include, but are not limited to, a lipase, a phosphatase, an amylase, a cellulase, a protease a peptidase, a urease or a deaminase. Specific examples of suitable hydrolases include, but are not limited to, organophosphorus hydrolase, organophosphorus acid anhydrolase, urease, butyrylcholinesterase or acetylcholinesterase. One or a plurality of types of enzymes can be incorporated within the polymer to detect one or a plurality of analytes. Examples of pH-sensitive dyes suitable for use with such enzymes include, but are not limited to, Brilliant green, crystal violet, methyl green, picric acid, Eosin Y, thymol blue, xylonel blue, Eosin B, cresol red, methyl yellow, ethyl orange, bromocresol green, Alizarin Red, bromomethyl blue, bromocresol purple, phenol red, and chlorophenol red.

In general, any enzyme and indicator compound (or compounds) combination that interact to produce a measurable change of state can be used in the polymers of the present invention. For example, 2,2'Dipyrdyl indicator dye changes color in the presence of $Fe^{2+}$. Thus, any enzyme using $Fe^{2+}$ as a substrate or producing $Fe^{2+}$ in a product can be used in conjunction therewith. Likewise, Calcium Green-1 and Fluo-3 AM (available from Molecular Probes, Inc.) undergo a color change in the presence of $Ca^{2+}$. Enzymes using $Ca^{2+}$ using or producing $Ca^{2+}$ during catalysis can be used with these dyes. For example, calmodulin is a calcium-binding protein exhibiting a calcium affinity which is dependent upon environmental conditions. As conditions change calmodulin binds either more or less calcium. Therefore polymers containing calmodulin and Ca2+ dye can be used as an environmental sensor. Many other enzymes affect concentrations of peroxide in an environment. The concentration of peroxide in the environment can affect the color of a dye (for example, by bleaching).

In another aspect, the present invention provides a process for preparing a sensor to detect the presence of at least one analyte as described above. The process comprises generally the steps of (a) incorporating into a polymer at least one enzyme that is selected to either (i) catalyze a reaction of the analyte to chemically convert the analyte to a product compound or (ii) be inhibited by the analyte in the presence of a substrate compound; and (b) incorporating into the polymer at least one indicator compound selected to produce a measurable change of state as a result of the interaction of the analyte and the enzyme.

In one embodiment, the enzyme and the indicator compound are incorporated into the polymer matrix during synthesis of the polymer. For example, polyurethane biosensor of the present invention above can be formed by mixing water, the enzyme, the indicator compound and an isocyanate functionalized polyurethane prepolymer. Incorporation of the enzyme(s) and indicator compound(s) into the polymer network In still another aspect, the present invention provides a method for detecting the presence of at least one analyte. The method includes the step of exposing a sensor to an environment in which the analyte is present. As described above, the sensor includes at least one enzyme that is selected to either (i) catalyze a reaction of the analyte to chemically convert the analyte to a product compound or (ii) be inhibited by the analyte in the presence of a substrate compound. The sensor also includes at least one indicator compound selected to produce a measurable change of state as a result of the interaction of the analyte and the enzyme. Each of the enzyme and the indicator compound are incorporated within a single polymer. The method preferably further comprises the step of measuring the change of state (for example, viewing a color change).

In an additional aspect, the present invention provides a polymeric sensor operable to indicate the presence of an enzyme. The sensor includes at least one substrate compound and at least one indicator compound selected to produce a measurable change of state as a result of the interaction of the substrate and at least one target or analyte enzyme. As described for the sensors above, each of the indicator(s) and substrate(s) are incorporated within a single polymer. This sensor makes use of enzyme-substrate interactions to facilitate a change in the indicator compound as described above. The sensor can, for example, be used to detect the presence of enzymes using polymerized enzyme substrates.

In a further aspect, the present invention provides a process for preparing a sensor to detect the presence of at least one analyte enzyme comprising the steps of: incorporating at least one substrate compound that is selected to react in a reaction catalyzed by the analyte enzyme and incorporating into the polymer at least one indicator compound selected to produce a measurable change of state as a result of the interaction of the analyte enzyme and the substrate compound.

In still a further aspect, the present invention provides a method for detecting the presence of at least one analyte enzyme including the steps of: (a) exposing a sensor to an environment in which the analyte enzyme is present, the sensor including at least one substrate compound that is selected to react in a reaction catalyzed by the analyte enzyme and at least one indicator compound selected to produce a measurable change of state as a result of the interaction of the analyte enzyme and the substrate compound, each of the substrate compound and the indicator compound being incorporated within a single polymer; and (b) measuring the change of state.

In the case that the indicator compound(s) of the present invention undergoes a visible transition during enzyme catalysis of a target analyte or substrate, the need for cumbersome electrical equipment, electrodes, or special devices associated with prior enzymatic sensors is eliminated. In general, any compound that undergoes or produces an measurable transition in the presence of a reaction product is preferred for use in the present invention. Such compounds are referred to generally herein as "dyes." As discussed above, the transition is preferably viewable by the "naked" human eye.

DETAILED DESCRIPTION OF THE INVENTION

Reactions catalyzed by hydrolase enzymes including, but not limited to lipases, phosphatases, amylases, cellulases, proteases, peptidases, ureases, and deaminases, change the pH of an environment as the reaction produces either hydroxyl or hydronium ions during substrate hydrolysis. Such enzymes were used as models in the studies of the present invention. These studies have shown, for example, that pH-sensitive dyes, when immobilized in the same polymer structure as hydrolase enzymes (or a substrate thereof), undergo the same pH transition within the polymer as occurs in aqueous solution. Once the pH of the reaction medium changes sufficiently, the polymer visibly changes color. The degree of color change can be correlated to the amount of hydrolysis of a particular substrate. Therefore, color change of varying degree not only indicates the presence of a particular substrate, but also the quantity of substrate present.

In a number of studies of the present invention, hydrolase enzymes were incorporated into polymers during polymer synthesis. There are numerous advantages with the this type of immobilization as compared to incorporation of enzymes into existing polymers as commonly practiced in the art. For example, if one desires to incorporate proteins into a microporous membrane, it is impossible to load the enzyme into the pores after membrane synthesis is complete. It is also advantageous to have immobilization occur in a single step.

Figure 1:
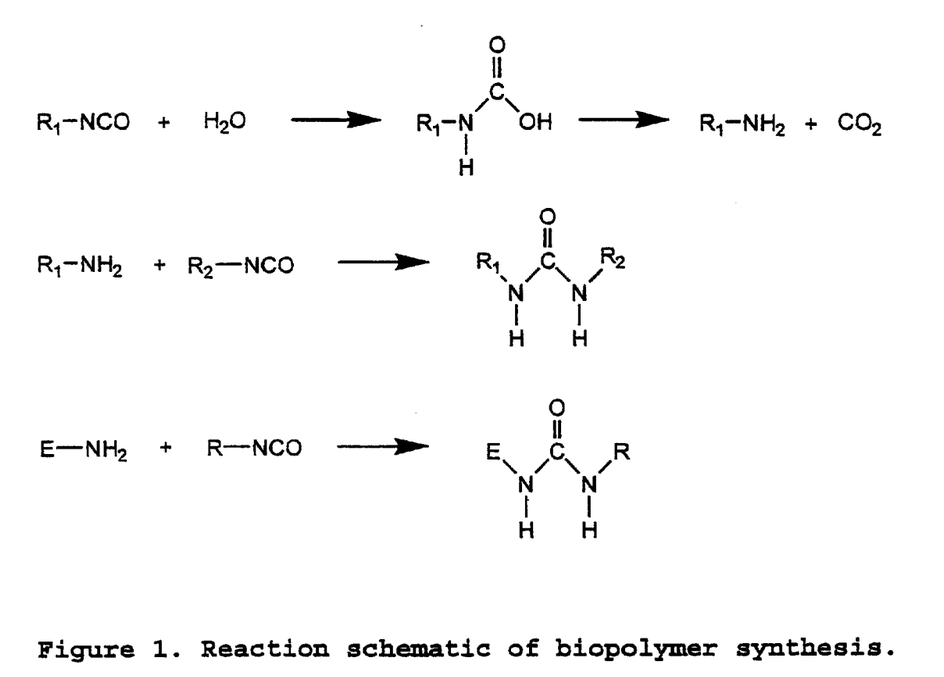
FIG. 1 illustrates an embodiment of a reaction schematic for biopolymer synthesis.

Polyurethanes were studied as a model system. Polyurethane foams are attractive support materials in part as a result of the synthetic route for producing such foams. One method of polyurethane synthesis entails the reaction of relatively hydrophilic polyurethane prepolymer with aqueous solution, resulting in a urethane foam. The polyurethane prepolymers used in the present studies were urethanes that had been capped (that is, functionalized at chain ends) with multiple isocyanate functionalities. As known in the art, prepolymers containing multiple isocyanate functionalities have the ability to form chemical crosslinks upon reaction with a diol or water. Water reacts with isocyanates, initiating a foaming reaction in which a carbamic acid intermediate is formed. The carbamic acid quickly degrades to an amine and evolves $CO_2$. The carbon dioxide bubbles through the highly viscous reacting polymer solution providing for a porous foam structure. Amines readily react with isocyanates; therefore, a multi-functional prepolymer in aqueous solution results in a crosslinked polyurethane matrix or network. Because the vast majority of enzymes are most active in aqueous solution, water not only serves to initiate the prepolymeric reaction, but also provides an effective route to deliver an enzyme to the reaction. Proteins, having many amine groups present via lysine residues, can readily react with isocyanate functionalities, theoretically forming a crosslinked polymer-protein network through multi-point attachments of the enzyme and polymer. A schematic of the reactions occurring in this process is shown in FIG. 1. In FIG. 1, $R_1$ represents a prepolymer molecule (for example, having a molecular weight of approximately 300 to approximately 10,000) having multiple isocyanate functionalities/groups. $R_2$ and R represent other prepolymer molecules with isocyanate functionalities. E represents an enzyme with a reactive amine functionality present via lysine residues and at the N-terminus of the protein.

Additionally, control of the porosity, foam cell structure, and swellability of such a system is facilitated by introducing additives such as surfactants which affect the process of $CO_2$ evolution and result in an alteration of foam surface properties. It is believed that surfactants stabilize the carbon dioxide bubbles that are formed during synthesis and are responsible for foaming. For example, certain surfactants have been found to promote the creation of small carbon dioxide bubble, resulting in formation of a polymer product having a morphology similar to a fabric. Other surfactant have been found to promote relatively large carbon dioxide bubbles, resulting in a polymer product having a morphology similar to a sponge. Given the control that surfactants enable over the physical/morphological characteristics of polyurethanes, suppliers of polyurethane prepolymer typically recommend that surfactant be added to a polyurethane reaction mixture.

Polyurethane biopolymer synthesis provides a relatively straightforward mechanism for the incorporation of dyes within the polymer composite material. In that regard, the isocyanate reaction is relatively non-specific and capable of covalently binding many different types of chemical functionalities present on a dye. These functionalities include, for example, amines, hydroxyls, carboxylic acids, urea, amides, and phenols. The polymerization also permits physical entrapment of dyes not containing functionality with reactivity toward isocyanates. Physical entanglements and favorable hydrophobic interactions facilitate retention of dyes in the absence of covalent modification/linkage.

In one embodiment of the present invention, hydrolytic enzymes and dyes were incorporated within a polyurethane polymer matrix for use in the detection of enzyme substrates and inhibitors. Such a substrate or inhibitor can, for example, be within a solution or on a surface. To characterize the invention, several enzymes and various dyes were incorporated within polyurethane polymers during polymer synthesis. The enzyme polymers were then analyzed for catalytic activity and efficiency in detection. The data indicate that detection of even small quantities of enzyme substrate and/or inhibitor is possible with the use of these novel materials. As clear to one skilled in the art, the lower limit for detectable concentrations of analyte using the sensors of the present invention is dependent upon the enzyme used, whether the analyte is an indicator or substrate, and the affinity of the enzyme for the analyte or other substrate (in the case that the analyte is an inhibitor). The inhibitor di-isopropyl fluorophosphates, for example, has been detected as sub-micromolar concentrations using immobilized burytylcohlinesterases in the present invention.

EXPERIMENTAL PROCEDURES

1. Enzyme and Dye-Containing Polymer Synthesis

As known in the art, variations of the reaction conditions during synthesis of polyurethanes affect both the physical properties of the resultant foam as well as the degree of enzyme-foam interaction. Described below is a typical procedure for biopolymer synthesis. Initially, 4 ml of pH 7.8 Tris buffer (10 mM) containing Pluronic F-68 surfactant (0.8 to 1 wt %) and dye (10 mg nitrazine yellow) were placed into a narrow cylindrical mixing vessel. Subsequently, an enzyme solution (for example, 1 ml of 1.5 mg/ml urease in the same buffer) was added. Finally, approximately 4 ml of Hypol™ prepolymer, available from Hampshire Chemical Corp., a subsidiary of The Dow Chemical Company, (preheated to 30° C. to limit handling problems due to high viscosity) were added to the mixture. The solutions were then intimately mixed. During the initial "cream" period, the solution was injected into a cylindrical mold where it rose and then set within 2 to 5 minutes. Polymer synthesis was complete in less than 10 minutes. The $CO_2$ evolved during the reaction of water and isocyanate lifted the foam to a final volume of approximately 50 to 60 ml.

After the initial 10 minute "set-up" time, foam samples were treated in several ways. Some foam samples were immediately sealed in vials, while others were pre-rinsed. Bulk foam samples were usually placed in a fume hood or lyophilizer to facilitate the removal of residual water and $CO_2$ still present from the reaction. Foams were stored under a wide range of conditions until being assayed for enzyme activity.

The mixing system used in the studies of the present invention required 30 to 40 seconds of mixing at 2500 rpm to create a high quality foam with Hypol 3000, a toluene di-isocyanate based prepolymer. The mixing system included an oar-shaped metal loop having a height of 3.2 cm and a diameter of 1.3 cm. Hypol 5000 (methylene bis(p-phenyl isocyanate) based), a more hydrophobic prepolymer, required additional mixing. Insufficient mixing leaves un-reacted residual prepolymer dispersed within a dense hard mass of polyurethane. Overmixing does not allow the evolving $CO_2$ to act in lifting the foam. Properly mixed foam will generally increase approximately 6 fold in volume throughout the course of the reaction.

In general, an aqueous solution of enzymes and environmentally sensitive dyes were contacted with an isocyanate-based prepolymer under sufficient agitation to initiate reaction. The enzyme may, for example, be added as a freeze-dried powder or aqueous solution that is either pure or impure. The term "impure" a used herein refers to enzymes containing, for example, other proteins/enzymes and biological molecules. Virtually any protein, enzyme or combination of proteins and/or enzymes can be co-immobilized within the same polymer.

In model studies of the present invention, dye-containing polymers both with and without enzyme(s) were synthesized. Enzymes studied included organophosphorus hydrolase (OPH), organophosphorus acid anhydrolase (OPAA), urease, butyrylcholinesterase, and acetylcholinesterase. The efficacy of using the enzyme/dye-containing polymers of the present invention in sensing applications was demonstrated with a series of substrate and inhibitor solutions including paraoxon, parathion, diisopropyl fluorophosphate, urea, urine, butyrylcholine, and acetylcholine. The details of these experiments and procedures employed therein are described below.

2. Color-Dependence of pH Sensitive Dye Containing Polymers

Using the procedures for polymer synthesis described above, nitrazine yellow dye-containing polymers were synthesized having a dye content of approximately 0.4 mg dye/g dry polymer. Physical property differences clearly visible to the naked human eye occurred when the polymers were incubated within aqueous solutions of varying pH. The color of the samples range from bright orange at pH 6.5 to blue at pH 9.0. Distinctions in color were clearly discernable to the naked eye between each of samples exposed to a pH of 6, 6.4, 6.8, 7.2, 7.6, 8, 8.5 and 9. The series of colors observed in the polymers of the present invention was the same as the series of colors that is produced by suspending the soluble dye within aqueous solution over the same pH range. In general, therefore, the resolution of the polymers sensors of the present invention is generally the same as the indicator compound or dye immobilized therein with respect to differences in pH and differences in analyte concentrations associated therewith.

3. pH Changes Incurred by Enzyme Catalysis

Figure 2A:
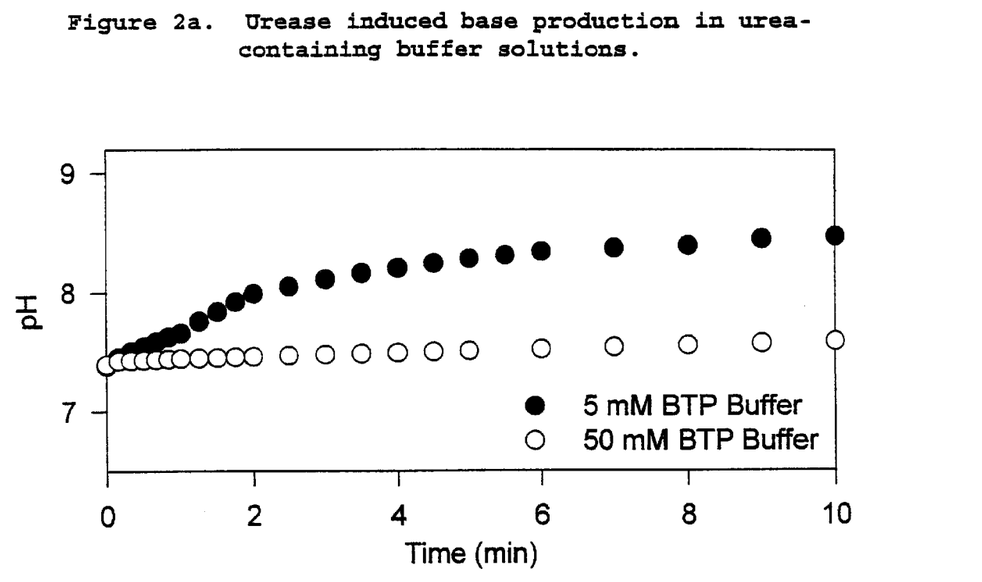
FIG. 2a illustrates urease-catalyzed production of base in an aqueous solution of urea.
Figure 2B:
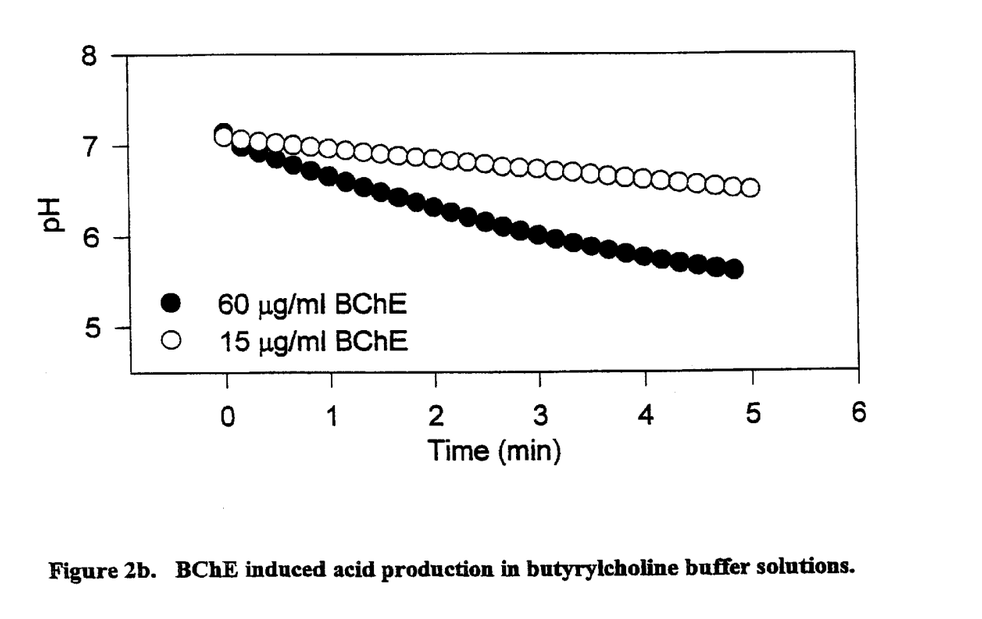
FIG. 2b illustrates butyrylcholinesterase-catalyzed production of base in a butyrylcholine solution.

Buffers are commonly employed when using enzymes within a process environment to protect enzymes from pH-induced denaturation as catalysis proceeds. In the case of a biosensor application, however, the biosensor may use pH changes for detection. FIGS. 2a and 2b illustrate the pH changes incurred when utilizing urease and butyrylcholinesterase enzymes within dilute buffered solutions of their appropriate substrates. FIG. 3a demonstrates that high buffer capacity of solution masked base production. The pH of the 50 mM Bis-Tris Propane (BTP) buffer solution did eventually increase at a rapid rate after the base production exceeded the solution's buffer capacity. FIG. 3b illustrates that the rate of pH change induced by butyrylcholine hydrolysis was directly related to BChE concentration within a particular solution (10 mM Phosphate buffer pH 7.2).

4. Urease-Polymer Catalyzed Urea Hydrolysis (Substrate Detection)

Urease (3 mg/g polymer) polyurethane copolymers containing pH sensitive dye (2 mg/g polymer) were synthesized using the synthesis procedures described above. The resultant polymers were sliced into 150 mg disks. The disks were then incubated in differing solutions (2 ml) to demonstrate polymer selectivity in detecting the enzyme's substrate. Color changes (or lack thereof) of the polymer disks were recorded at 10 minutes and at 40 minutes after the solution application. Several polymer disks were incubated in 50 mM phosphate buffer containing urea (400 mM). Phosphate buffer (50 mM) alone was applied to several other samples, while untreated tap water was applied to still other samples. The polymer disks incubated in 50 mM phosphate buffer containing urea (400 mM), clearly indicate the presence of urea in solution by undergoing a transition from yellow to blue while the other polymer disks (incubated in phosphate buffer and untreated tap water) retained the yellow color. The color transition in the polymer disks incubated in 50 mM phosphate buffer containing urea was a result of an increase in pH brought on by urea hydrolysis and subsequent response of the immobilized m-cresol purple dye.

5. Butyrylcholinesterase Polymer Detection of Dimethyl Methylphosphonate (Inhibitor Detection)

Human butyrylcholinesterase was co-immobilized within polyurethane polymers along with nitrazine yellow dye. The polymers (150 mg disks) were incubated (2 ml) with various concentrations of dimethyl methylphosphonate (DMMP), for thirty minutes. A concentrated solution (2 ml) of the enzyme's substrate (50 mM butyrylcholine) was then applied to each disk. As butyrylcholinesterase catalyzes substrate hydrolysis, the pH was reduced and the polymers underwent a transition from bluish-brown to orange. To remove subjectivity from the experimental procedures, a solid-phase Minolta CM-500d spectrophotometer was used to monitor the color change of the biocatalytic polymers. The spectrophotometer uses a three-dimensional color coordinate system (L*a*b) to define colors and intensity. In this coordinate system, well defined colors are placed at the ends of each axis: yellow at −b and blue at +b; green at −a and red at +a; and black at −L and white at +L. Any color can be defined at some position within the resultant three-dimensional space. The nitrazine dye that was employed in these assays undergoes a transition from brownish-blue at alkaline pH to orange when acidic, therefore the largest change in the L*a*b coordinate system during an assay occurred along the b-directional axis. Each kinetic reaction was performed in duplicate.

Figure 3:
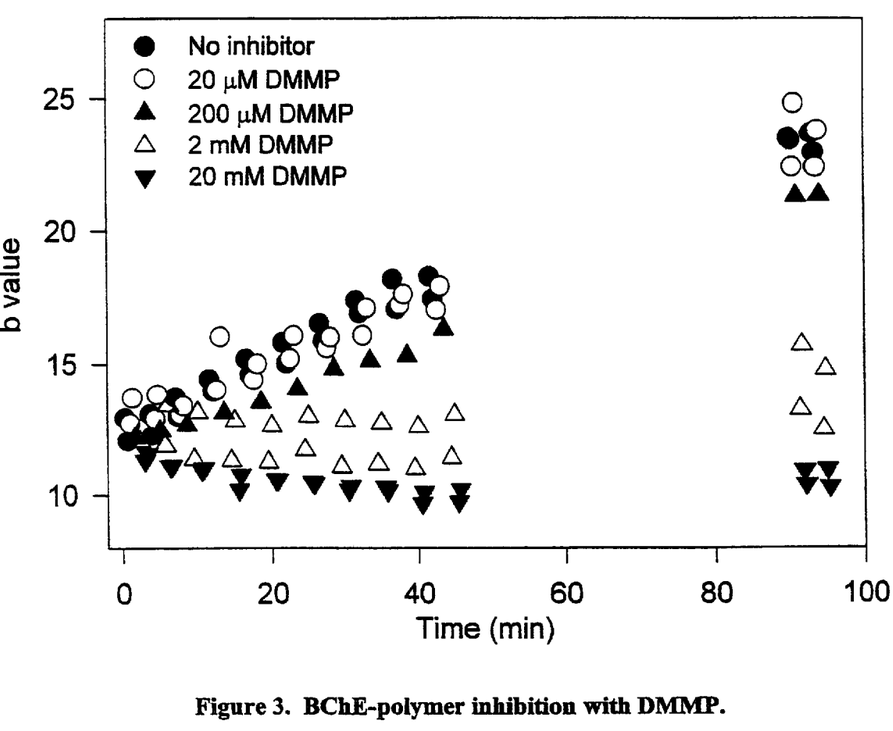
FIG. 3 graphically illustrates data from a solid's spectrophotometer which indicate dimethyl methylphosphonate inhibition of butyrylcholinesterase polymers.

FIG. 3 and Table 1 set forth the rate data observed in this inhibition experiment. DMMP is an effective inhibitor of immobilized butyryl cholinesterase, resulting in a complete loss of enzyme activity at a concentration of 20 mM.

TABLE 1

Rate data for DMMP inhibited BChE-polymers

| DMMP Concentration | 0 μM | 20 μM | 200 μM | 2 mM | 20 mM |
|---|---|---|---|---|---|
| Reaction rate (Δb/min) | 0.119 | 0.113 | 0.086 | 0.020 | −0.005 |
| Activity retention (%) | 100 | 95 | 73 | 27 | 0 |

6. Detection of Galactosidase Activity Using a Substrate-Containing Polymer (Enzyme Detection)

Ortho-nitrophenol-β-d-galactopyranoside (ONPG) was directly polymerized within polyurethane polymers using synthesis techniques described above. In this example, the ONPG is both a substrate compound and an indicator compound as it changes color during hydrolysis. Resulting polymers were vigorously washed in dilute phosphate buffer to ensure that any non-covalently incorporated ONPG was rinsed from the polymers. Increasingly dilute solutions of galactosidase solutions were applied directly onto the washed polymer samples. Table 2 provides the amount of galactosidase activity that was initially applied to each polymer disk (~200 mg). Table 2 also shows the colormetric response observed on the polymer disks. Color values in Table 2 are L-parameter values within an L-a-b color coordinate system, which were attained using a solid-phase spectrophotometer (calorimeter), as described above. As expected, the degree of color response achieved in a sample was directly proportional to the amount of enzyme activity applied to a given polymer disk. After 90 minutes all of the disks, except for a control in which no galactosidase was applied, were bright yellow.

TABLE 2

Solid spectrophometer detects breadth of color development in polymer sensors.

| Disk No. | 1 | 2 | 3 | 4 | 5 | 6 | 7 | 8 |
|---|---|---|---|---|---|---|---|---|
| Galactosidase Applied (units) | 13.2 | 6.6 | 3.3 | 1.65 | 0.83 | 0.41 | 0.21 | 0.10 |
| Color value at 25 minutes | 0.11 | 1.81 | 2.14 | 3.34 | 5.95 | 9.41 | 10.99 | 16.30 |

7. Detection of Compounds Adsorbed onto a Surface.

Paraoxon, a cholinesterase inhibitor, was solublized within methylene chloride at 34 mM concentration. A small amount (0.5 ml) of the solution was placed within 150 ml glass beakers. The same volume of methylene chloride (without paraoxon) was placed within a set of experimental control beakers. The methylene chloride was evaporated under forced convection.

Figure 4:
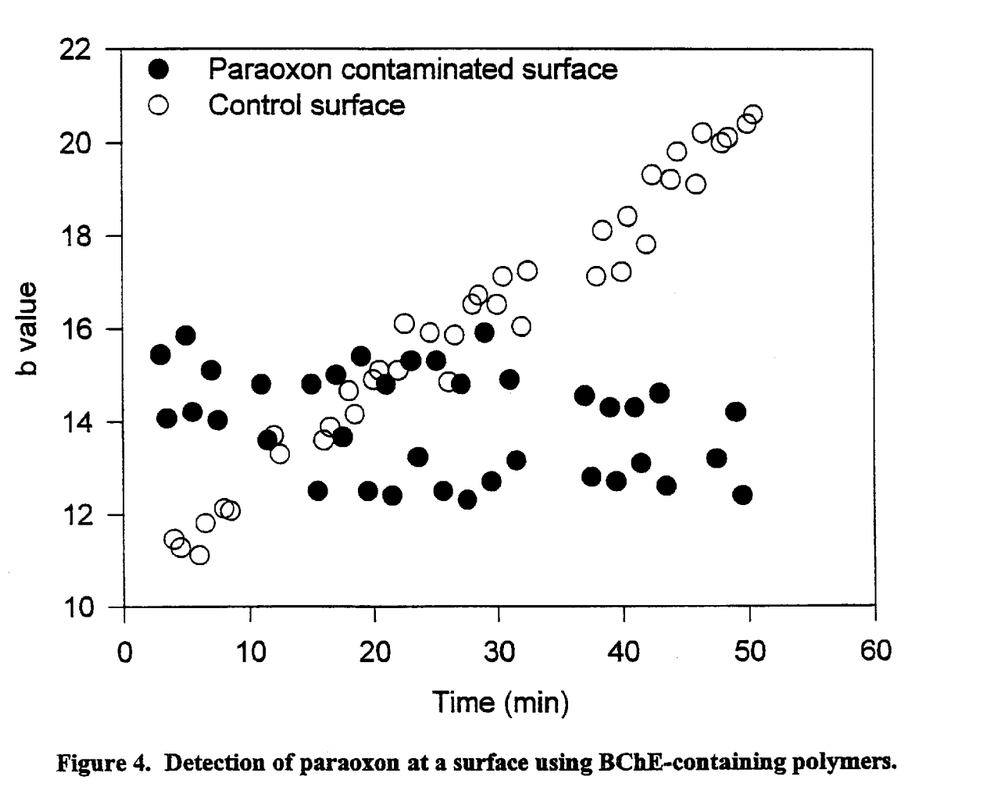
FIG. 4 graphically illustrates spectrophotometric data indicating surface detection of paraoxon with butyrylcholinesterae and dye containing polymers.

Butyrylcholinesterase and nitrazine yellow dye-containing polymers (150 mg) were used to wipe the bottom surface of the beakers. The polymer samples were then incubated within (2 ml) buffer (phosphate 1 mM pH 7.2) for 30 minutes to standardize the assay and afford the enzyme with the opportunity to become inhibited. An aqueous solution of butyrylcholine (25 mM) within the same buffer was then applied to each disk to initiate enzyme reaction. The solid-phase Minolta CM-500d spectrophotometer was again used to quantify color changes in the samples (See FIG. 4). The samples used to wipe the paraoxon-containing beakers displayed complete inhibition and underwent no color change at all in the presence of butyrylcholine, while those used on the control beakers became bright orange in minutes.

Although the present invention has been described in detail in connection with the above examples, it is to be understood that such detail is solely for that purpose and that variations can be made by those skilled in the art without departing from the spirit of the invention except as it may be limited by the following claims.

What is claimed is:

1. A sensor for detecting the presence of at least one analyte enzyme in an environment, the sensor comprising:
at least one substrate compound that is selected to react in a reaction catalyzed by the analyte enzyme; and
at least one indicator compound selected to produce a measurable change of state as a result of the interaction of the analyte enzyme and the substrate compound;
each of the substrate compound and the indicator compound being incorporated within a single polymer.

2. The sensor of claim 1 wherein the indicator compound is a dye that changes optical properties as a result of the interaction of the analyte enzyme and the substrate compound.

3. The sensor of claim 2 wherein the polymer matrix comprises a polyurethane.

4. The sensor of claim 3 wherein the substrate compound is covalently bonded to the polyurethane.

5. The sensor of claim 4 wherein the indicator compound is entrapped within the polyurethane.

6. The sensor of claim 4 wherein the indicator compound is covalently bonded to the polyurethane.

7. The sensor of claim 3 wherein the analyte enzyme is a hydrolase enzyme and the dye changes color as a function of pH.

8. The sensor of claim 7 wherein the hydrolase enzyme is a lipase, a phosphatase, an amylase, a cellulase, a protease a peptidase, a urease or a deaminase.

9. The sensor of claim 8 wherein the hydrolase enzyme is organophosphorus hydrolase, organophosphorus acid anhydrolase, urease, butyrylcholinesterase or acetylcholinesterase.

10. A process for preparing a sensor to detect the presence of at least one analyte enzyme comprising the steps of:
incorporating at least one substrate compound that is selected to react in a reaction catalyzed by the analyte enzyme; and
incorporating at least one indicator compound selected to produce a measurable change of state as a result of the interaction of the analyte enzyme and the substrate compound into the polymer.

11. The process of claim 10 wherein the substrate compound and the indicator compound are incorporated into the polymer during synthesis of the polymer matrix.

12. The process of claim 11 wherein the polymer is a polyurethane.

13. The process of claim 12 wherein the polyurethane is formed by mixing water, the substrate compound, the indicator compound and an isocyanate functionalism polyurethane prepolymer.

14. The process of claim 13 wherein the analyte enzyme is a hydrolase enzyme and the indicator compound is a dye that undergoes an observable color change as a function of pH.

15. A method for detecting the presence of at least one analyte enzyme, the method comprising the steps of:

exposing a sensor to an environment in which the analyte enzyme is present, the sensor including at least one substrate compound that is selected to react in a reaction catalyzed by the analyte enzyme, the sensor further including at least one indicator compound selected to produce a measurable change of state as a result of the interaction of the analyte enzyme and the substrate compound, each of the substrate compound and the indicator compound being incorporated within a single polymer; and measuring the change of state.

* * * * *

UNITED STATES PATENT AND TRADEMARK OFFICE
CERTIFICATE OF CORRECTION

PATENT NO. : 6,673,565 B2 Page 1 of 1
DATED : January 6, 2004
INVENTOR(S) : Keith E. Lejeune and Alan J. Russel

It is certified that error appears in the above-identified patent and that said Letters Patent is hereby corrected as shown below:

<u>Column 1,</u>
Line 8, add the following text after "RELATED REFERENCE" and before "BACKGROUND OF THE INVENTION":
-- GOVERNMENT INTEREST This invention was made with Government support under Contract No. DAAD19-01-C-0043 awarded by the Department of Defense. The Government has certain rights in the invention. --

Signed and Sealed this

Thirty-first Day of August, 2004

JON W. DUDAS
*Director of the United States Patent and Trademark Office*